United States Patent
Postaire et al.

(10) Patent No.: US 6,399,055 B1
(45) Date of Patent: Jun. 4, 2002

(54) METHOD AND COMPOSITION FOR TREATMENT OF INFANT DIARRHEA

(75) Inventors: Eric Postaire, Vanves; Christine Bouley, Vaucresson; Corinne Guerin-Danan; Claude Andrieux, both of Paris, all of (FR)

(73) Assignee: Compagnie Gervais Danone, Levallois-Perret (FR)

( * ) Notice: Subject to any disclaimer, the term of this patent is extended or adjusted under 35 U.S.C. 154(b) by 0 days.

(21) Appl. No.: 09/179,179

(22) Filed: Oct. 27, 1998

(51) Int. Cl.$^7$ .............................. A01N 63/00; C12N 1/20
(52) U.S. Cl. ...................... 424/93.45; 424/439; 426/61; 435/252.9
(58) Field of Search .............................. 424/439, 93.45, 424/93.4, 435; 426/72, 61; 435/252.9

(56) References Cited

U.S. PATENT DOCUMENTS 5,837,238 A * 11/1998 Casas et al. ............. 424/93.45

FOREIGN PATENT DOCUMENTS

| WO | WO 96/20607 | | 7/1996 |
|---|---|---|---|
| WO | WO-96-20607 | * | 7/1996 |

OTHER PUBLICATIONS

Danone World Newsletter No. 7, Jan. 1995, Introduction, pp. 1–2; Table 1, p. 1.*
Isolauri E. et al, Pediatrics Biosis, 1991.*
Am. J. Clin. Nutr. 1998;67:111–7, Guerin–Danan, et al., Milk Fermented With Yogurt Cultures And Lactobacillus Casei Compared With Yogurt And Gelled Milk: Influence On Intestinal Microflora In Healthy Infants.
Vet. Pathol. 23:443–453 (1986), Johnson, et al., A Scanning And Transmission Electron Microscopic Study Of Rotavirus–Induced Intestinal Lesions In Neonatal Gnotobiotic Dogs.
Pediatric Research, vol. 22, No. 1, pp. 72–78 (1987), Heyman, et al., "Intestinal Absorption Of Macromolecules During Viral Enteritis: An Experimental Study On Rotavirus––Infected Conventional And Germ–Free Mice".
Dissertation Abstracts International, vol. 55, No. 2, pp. 484–485, (1994), Yliopisto, et al., "Immune Responses Evoked By Cow Milk Products In Health And During Rotavirus Diarrhea".
Asia Pacific J. Clin. Mutr. (1996) 5:53–56, Salminen, et al., "Probiotics And Stabilisation Of The Gut Mucosal Barrier".
Pediatric Research, vol. 33, No. 6 (1993), pp. 548–553, Isolauri, et al. "Diet During Rotavirus Enteritis Affects Jejunal Permeability To Macromolecules In Suckling Rats".
Jount Of Pediatric Gastronuerology And Nutrition, 20:333–338 (1995), Majamaa, et al., "Lactic Acid Bacteria In The Treatmetn Of Acute Rotavirus Gastroenteritis".
IDF Nutrition Newsletter 3, Salminen, et al. "Fermented Dairy Products, Intestinal Microflora And Health".
The Lancet, vol. 344, Oct. 15, 1994, pp. 1046–1049, Saavedra, et al. "Feedling Of Bifidobacterium Bifidum And Streptococcus Thermophilus To Infants In Hospital For Prevention Of Diarrhea And Shedding of Rotavirus".
Nutrition Today Supplement, vol. 31, No. 6, Nov./Dec. 1996, Kaila, et al., "Nutritional Management Of Acute Diarrhea".
Pediatrics, vol. 88, No. 1, Jul. 1991, pp. 90–97, Isolauri, et al., "A Human Lactobacillus Strain (Lactobacillus Casei SP Strain GG) Promotes Recovery From Acute Diarrhea In Children".
Biotherapy 8:129–134, 1995, pp. 129–134, Gonzalex, et al., "Biotherapeutic Role Of Fermented Milk".
Microbiologie Aliments Nutrition 1990, vol. 8, pp. 349–354, Gonzalez, et al., "Prevention Of Infantile Diarrhea By Fermented Milk".

* cited by examiner

Primary Examiner—Irene Marx
(74) Attorney, Agent, or Firm—Oblon, Spivak, McClelland, Maier & Neustadt, P.C.

(57) ABSTRACT

L. casei DN 114-001 is a bacterial agent known for its utility in the fermentation of milk products. A fermented milk product comprising as the sole bacterial agent L. casei DN 114-001 is effective in reducing the number of rotavirus associated diarrhea episodes experienced by infants up to 24 months of age. In particular, the number of rotavirus associated diarrhea episodes, as well as their severity and duration is reduced in children receiving milk products fermented with L. casei DN 114-001, present in the fermented milk product in amounts of at least $10^6$ CFU/g. L. casei may be the sole bacterial agent present in the fermented milk product, and yet effective reduction of diarrhea episodes associated with rotavirus infection is obtained.

15 Claims, 3 Drawing Sheets

THEY WERE INOCULATED AT 5 DAYS OF AGE WITH SA11 ROTAVIRUS ▨ OR MEM AS CONTROL ☐

THEY WERE INOCULATED AT 5 DAYS OLD WITH SA11 ROTAVIRUS OR MEM AS CONTROL

METHOD AND COMPOSITION FOR TREATMENT OF INFANT DIARRHEA

BACKGROUND OF THE INVENTION

1. Field of the Invention

This invention pertains to a composition comprising an effective amount of a publically available bacterial strain, *Lactobacillus casei* strain DN 114-001 as an aid to resisting rotavirus infection and diarrhea associated therewith, as well as reducing the severity and persistence of rotavirus diarrhea, in children up to 24 months of age. The invention also pertains to a method of supplementing the nutrition of infants up to 24 months of age with a fermented milk product fermented by *L. casei* DN 114-001 on a daily basis, as a diarrhea preventive, and in an effort to reduce frequency, severity and duration of diarrheal episodes. Importantly, *L. casei* DN 114-001 is effective, alone, as the sole bacterial agent in addressing diarrhea in infants up to 24 months of age.

2. Background of the Prior Art

Group A rotavirus is the leading cause of diarrhea among children aged 6 to 24 months worldwide. Rotavirus associated diarrhea causes 870,000 deaths/year principally in developing countries (1). Symptoms are watery diarrhea, frequently associated with severe dehydration (2) and malabsorption of nutrients (3, 4). Limited investigations by mucosal biopsy of infected infants have shown that rotavirus principally infects the cells of the small intestine. Introduction of fermented milk products in infant diet has been proposed for the prevention or treatment of acute diarrhea (4, 5–10). These products contribute to a well balanced diet and contain lactic acid bacteria (LAB) which are known for their healthful influence, especially in infants (11). Clinical and experimental studies have reported preventive and protective effects of LAB consumption on rotavirus diarrhea. Incidence of diarrhea and rotavirus shedding have been reduced in infants receiving the bacterial association *Streptococcus thermophilus* and *Bifidobacterium bifidum* (12). After oral rehydration, a significant reduction of diarrheal symptoms have been observed when infants consumed *Lactobacillus casei* strain GG (13–15), *Lactobacillus reuteri* (15) or a milk fermented by *Bifidobacterium longum* (16). The mechanisms involved in this protection remain poorly understood.

In a previous study, we have developed a germ-free suckling rat model to study group A rotavirus associated diarrhea (17). In this model, 5-day old infected rats developed a 6-day diarrhea characterized by watery feces containing rotavirus antigens. Histological analyses have demonstrates that rotavirus infects enterocytes and induces cellular vacuolation in the small intestine. Clinical and histopathological analyses were assessed in infected suckling rats supplemented by a milk fermented by the *Lactobacillus casei* strain DN 114-001, which has been previously involved in a beneficial effect on diarrhea in children (18).

SUMMARY OF THE INVENTION

Infants of age up to 24 months experience a transitioning diet, which typically proceeds from mother's milk or a formula substitute therefore, to soft and semi-soft cereals, to a wide variety of liquid, soft and hard foods at the upper range of the age bracket addressed herein. Applicants' invention resides in the discovery that a diet nutrient, comprising a bacterial agent wherein the bacterial agent consists of *Lactobacillus casei* strain DN 114-001 is an aid in preventing the occurrence of rotavirus infection-associated diarrhea, reducing its severity and reducing its duration. The nutrient supplement is preferably a fermented milk product containing viable *L. casei* strains in the amount of at least $10^6$ CFU/g, preferably at least $10^8$ CFU/g and most preferably at least $10^{10}$ CFU/g. Daily doses of 10–20 grams/kg body weight for a concentration of $10^8$ CFU/g are demonstrated effective in the treatment of rotavirus associated diarrhea. Preferably, at this concentration, a daily dose of 10–15 g/kg is administered.

The *L. casei* strain DN 114-001 is a publically available bacterial strain and it may a be readily obtained from the CNCM, Institute Pasteur, 25 Rue du Docteur Roux, Paris, France, under accession number I-1518. This deposit is made pursuant to Budapest Treaty Conditions, and all reservations as to its availability have been irrevocably removed. DN 114-001 is also present in the product Actimel, together with other bacterial agents, in Europe.

The preparation of milk fermentation products is known, per se, and does not constitute an aspect of the invention. Any fermented milk product which does not otherwise aggravate digestion, or present digestion problems, fermented by *L. casei* DN 114-001 is acceptable.

It is to be noted that the invention resides in the recognition that *L. casei* DN 114-001 is, in and of itself, an effective bacterial agent for the treatment of rotavirus-associated diarrhea. While this agent may optionally be combined with other bacterial agents, such as the 4-strain agent of French Patent Publication 2,739,869 dated Apr. 18, 1997, Applicants are the first to identify this specific strain as effective alone in preventing diarrhea, and reducing its severity, in infants up to 24 months of age.

DETAILED DESCRIPTION OF THE INVENTION

Figure 1:
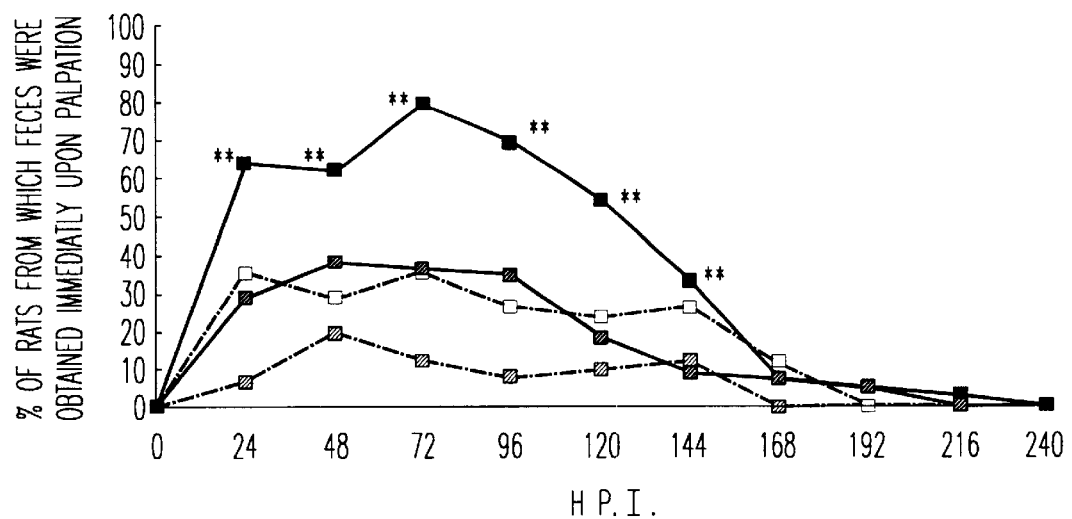
FIG. 1 compares the effectiveness of supplementation of diet with milk products fermented with *L. casei* DN 114-001, as compared to a non-fermented milk control product.

This invention contemplates a treatment, in the form of food supplementation, of the diet of an infant up to 24 months of age with a milk product fermented by *L. casei* DN 114-001. In infants receiving an infant formula product, or other "single bottle" nutrient, this diet supplement may be added to the preparation directly, or fed separately. Other infants, receiving either breast milk, or food from a variety of sources, may be supplemented according to this invention by direct feedings of a milk product fermented by *L. casei* DN 114-001, or by admixing that fermented milk product with other nutritional preparations.

Importantly, *L. casei* is demonstrated in protecting against rotavirus-associated diarrhea, and the severity of the diarrhea experienced. While there are numerous sources of diarrhea, rotavirus-associated diarrhea is a particularly severe and wide spread problem.

The fermentation product of this invention may be prepared in a fashion similar to that described in WO 96-20607, dated Jul. 11, 1996. Therein, a melange of bacterial agents is required to treat diarrhea. While one of the agents may be *L. casei* DN 114-001, the present invention may be distinguished therefrom because WO 96-20607 requires the use of a combination of four bacterial agents (*Streptococcus thermophilus* DN-001 147, *Streptococcus thermophilus* DN-001 339, *Lactobacillus bulgaricus* DN-100 182 and optionally *Lactobacillus paracasei subsp. paracasei* DN- 114 001) to suppress diarrhea incidents and severity. In contrast, the present invention resides in the discovery that *L. casei* DN 114-001, alone, is effective in treating diarrhea in infants up to 24 months of age.

It is important that the fermentation product have a sufficient concentration of *L. casei* viable cells. Cells must survive transit from the mouth through the digestive system to the small intestine, where rotavirus infection appears to occur. An effective concentration may be as low as $10^6$ CFU/g. In a preferred embodiment, the concentration is $10^8$ CFU/g, and an alternate preferred minimum is $10^{10}$ CFU/g. *L. casei* is demonstrated to survive well in the small intestine.

This invention addresses both a food supplement, and a method of treating infants up to 24 months of age to prevent diarrhea and/or reduce its severity and duration. Preferably, administration comprises daily administration of the fermented milk product. Intermittent administration may be similarly effective in the reduction of diarrhea severity and persistence, thus administration once every other day, once every three days, with the periods between administration extended up to seven days, may be convenient for parents and other care givers, while providing a measurable improvement in reduction of diarrhea attacks, as well as their severity and persistence. Additionally, in the absence of pre-infection supplementation, upon determination that the infant is experiencing a diarrhea episode, immediate daily supplementation with the fermented milk product fermented by *L. casei* DN 114-001 is within the scope of the invention, as a method of reducing the severity and persistence of the diarrhea episode. This is also true for those infants receiving periodic administration.

The necessary amount of fermented milk product to be ingested will vary from individual to individual, but in general, guidelines can be established, such that a minimum of 10–20 grams/kg body weight, on a daily basis, should be received. It will be apparent that enhanced concentration of *L. casei* DN 114-001 in the fermented milk product may be traded off against the amount of fermented milk product consumed.

The fermented milk product comprising the active bacterial agent of this invention is intended fororal administration. The efficacy of this invention has been demonstrated by using a mammalian model previously developed. In this model, germ-free Fischer suckling rat pups are employed, and the product is administrated by the pups sucking the products on a daily basis. Studies have demonstrated the predictive strength of this mammalian model for humans.

EXAMPLES

This invention has been demonstrated by means of in vivo testing. The examples that follow are not intended to be limiting, and reflect but one embodiment of the invention.

Materials and Methods

Milk Products

Milk products were obtained from the CIRDC (International Research Center Daniel Carasso, Danone, France) every fortnight and were stored at 4° C. throughout the study. The fermented milk contained viable *L. casei* strain DN 114-001 ($10^8$ CFU/g). Non-fermented heat treated (120° C., 15 s) cow milk was used as control.

Virus Inoculum Preparation and Animal Infection

Rotavirus strain SA 11 was originally obtained from Dr. M. K. Estes (Baylor College of Medicine, Houston, Tex.) and prepared as described by Jourdan et al. (19). Briefly, the virus was propagated in fetal rhesus monkey kidney cells (MA 104) that had grown under $CO_2$ in MEM (Gibco, Cergy Pontoise, France) containing 2.75 g/L $NaHCO_3$. The infected cells were grown under $CO_2$ in MEM containing 0.35 G/L $NaHCO_3$ and supplemented with trypsin (0.5 µg/ml) and Hepes buffer (20 mM, pH 7.6). Pools of rotavirus for administration to rats were prepared from clarified MA 104 cell lysate and stored at −80° C. The in vitro infectious activity was determined using an under agar plaque assay.

Animals and Feeding Protocol

Germ-free Fischer rats were delivered and maintained in sterile isolators. Four groups of minimum 4 litters were housed in separate isolators. The groups RF (n=55) and RM (n=39) were infected by rotavirus and received respectively the milk fermented by *L. casei* or the non-fermented cow milk. The groups CF (n=34) and CM (n=40) were not infected and used as supplementation matched control groups. Pups received the milk products by daily sucking from the age of 2 to 10 days. They were inoculated at 5 days or age with a 0.1 ml single dose either of virus inoculum (1.6 $10^9$ PFU/ml Plaque Forming Unit/ml) or MEM as control. Inoculation was performed with a plastic Pasteur pipette (miniliquipette, Prolabo, France). After inoculation, infant rats were returned to their dams and allowed to suckle.

Lactobacilli Numerations

The concentration of lactobacilli in the digestive tract was measured in 5-day old rats supplemented with the fermented milk from 2 days of age (n=6). The rats were sacrificed and intestinal segments were sterilely removed. Stomach, small intestine and colon were separately diluted in Liquid Casein Yeast extract (LCY) medium [casein enzymatic hydrolysate (USBC, Cleveland, Ohio, USA): 2 g/l, yeast extract (Difco): 2 g/l, NaCl: 5 g/l, KH2PO4: 1 g/l] and homogenized with an ultra-turrax. Serial dilution ($10^{-2}$–$10^{-5}$) were plated in MRS agar]55 g/l Man Rogosa and Sharpe (Difco)] and incubated at 30° C. during 5 days in aerobic conditions.

Diarrhea Examination

Pups were checked daily for diarrhea by gentle massage of their abdomen. Diarrhea was defmed when poorly formed yellow-green feces occurred immediately upon palpation. Control rats were treated identically to infected ones. Individual stool specimens were carefully collected in sterile plastic tubes on a weighted piece of plastic. Samples were stored at −80° C. before analysis.

Rotavirus Antigens Detection

Virus antigen was determined using a double sandwich ELISA (Enzyme-Linked Immunosorbant Assay). Microplates (Falcon 3915 probind) were coated overnight at 4° C. with a 1/1000 dilution of anti VP6 monoclonal antibodies (20) and saturated with 5% fetal calf serum. Samples were added to the plates and incubated for 1 h at room temperature. Rabbit antibodies to rotavirus were added to the washed plates, which were then incubated for 1 h at room temperature. The plates were washed again, and alkaline phosphatase-conjugated antibodies to rabbit IgG were added. The plates were incubated for 1 h at room temperature and washed. The reaction was terminated by adding a 1 g/L p-nitrophenyl phosphate solution (Sigma) in diethanolamine buffer (pH 9.8). Absorbency was measured at 400 nm using a spectrophotometer (Titertek multiscan MCC1340). Negative and positive control tests were included in each plate. Negative tests consisted on PBS and positive ones on a serial dilution of the viral inoculum [from $1.6C10^8$ to $1.9C10^5$ PFU/ml]. Each plate contained samples obtained from infected and non-infected pups of the same supplementation group. Assays were performed in duplicate. the cutoff OD value was 0.1. The viral antigen load in positive samples was determined relatively to the standard curve in each plate and the dilution of samples. In this assay we have been able to detect rotavirus antigen in virus stock titrating $10^6$ PFU/ml. Rotavirus shedding was determined by the viral antigen load measured in fecal samples diluted in 170 $\mu$l phosphate buffer. Rotavirus antigens were detected int eh intestine of pups every 3 h from 0 to 24 h p.i. and every 24 h from 24 to 120 h p.i. At each time point, 3 rats were sacrificed; the entire intestinal tract was removed and divided into stomach, small intestine and colon. For each part of the intestine, intestinal wall and contents were carefully separated, homogenized (Ultra-turrax, Bioblock, Paris, France) in sterile water and tested for rotavirus.

Histological Examination

The aspects of histological sections of the proximal small intestine was compared in each group. Three pups were sacrificed 2, 3 and 4 days p.i. Segments of the jejunum were removed. Fresh tissues were fixed in cooled ethanol as described by Sainte-Marie (21). They were then dehydrated and embedded in paraffin. paraffin sections (6 $\mu$m) were cut on a microtome (Leitz, Wetzlar, Germany) and were polychromatically stained. Acid, neutral and sulfated mucin were stained by alcian blue, periodic acid-Schiff and high iron diamine respectively. Cellular nuclei were strained by Hansens ferric trioxyhematein, muscular fibers by picric acid and collagen and basement membranes by indigocarmin. Care was taken that only longitudinal sections cut perpendicularly to the muscular mucosa were studies. The cell morphology was observed under light microscopy. Villi height, crypt depth, the number of mucus containing cells and the presence of vacuoles were determined on 10 different villi from the same intestinal section. The localization of the vacuoles was characterized at the apex or the basal zone of the villi. A vacuolation rate was defined as the percentage of villi in which vacuoles were observed.

Statistical Analyses

At each time point, analysis of variance was used for intergroup differences. Differences in percentages were evaluated with the Khi-square test. $P<0.05$ was considered significant.

Results

Lactobacilli Numeration

*L. casei* DN 114-001 survived throughout the intestinal transit as shown by the amount of bacteria recovered in the different parts of the digestive tract. Daily gavage of rats from 2 to 5 days of age maintained similar lactobacilli concentration in the stomach and the small intestine: respectively 3.8 log (CFU/g) and 3.5 log (CFU/g). In the colon, the concentration of lactobacilli was significantly higher: 5.7 log (CFU/g) ($p<0.05$).

Clinical Investigations

Diarrhea occurred in the infected rats supplemented with the non-fermented milk. The percentages of rats from which feces were immediately obtained upon palpation were significantly higher int he group RM compared with those obtained in the group CM from 24 to 144 h p.i. ($p<0.05$) (FIG. 1). In the group CM, less than 20% of pups delivered small and dark feces throughout the study, whereas the majority of the pups int eh group RM delivered diarrheal feces during this period. Fermented milk consumption decreased significantly the percentages of rats delivering feces in the group RF compared with those obtained from the group RM. No significant difference was observed between the groups RF and CF receiving the fermented milk. In these groups, the percentages of rats from which feces were immediately obtained were lower than 40% at each time point of the study. Even though the percentages of rats were significantly higher in the group CF compared with the group CM at 24, 72 and 96 h p.i., the feces consistency was similar. In the control groups the samples were not diarrheal and presented a brown color.

Rotavirus Detection

Immediately after infection, rotavirus antigens were detected in the stomach contents of both infected groups RM and RF (Table 1). From 3 h p.i. forward, rotavirus antigens were not detected in the stomach contents in the group RM. By contrast in the group RF, rotavirus antigens remained until 9 h p.i. The stomach wall was never infected. Rotavirus antigens were found in the small intestine, from inoculation to 120 h p.i. in the group RM. The intestinal mucosa was infected from 3 h p.i. in this group. In the group RF, positive intestinal samples were found from inoculation to 9 h p.i. The intestinal mucosa was also infected from 3 h p.i. but no rotavirus antigen was found from 48 h p.i. except in 1 rate 120 h p.i. Rotavirus antigens were detected in the colonic mucosa from 6 to 24 h p.i. in the group RM. In the group RF, viral antigens were found only in the colonic contents.

In fecal samples, rotavirus was detected within 5 and 6 days p.i. in the groups RF and RM respectively (Table 2). The proportion of samples in which rotavirus was detected was significantly lower in the group RF compared to the group RM at 2 days p.i. The load of rotavirus in the feces was systematically lower in the group RF. This difference was statistically significant at 3 d p.i. ($p<0.05$).

Histological Analyses

Figure 2A:
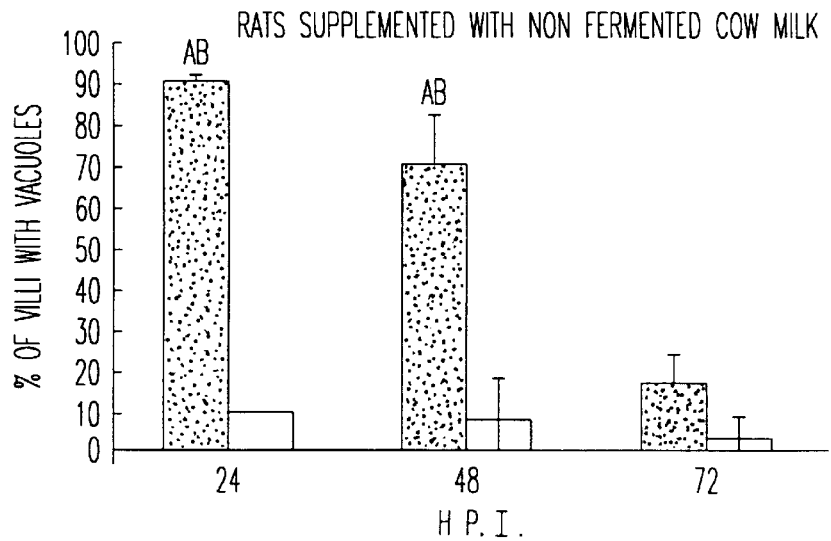
FIG. 2 is a graphic presentation of the relative presence of cellular vacuoles in the small intestinal villi of suckling rats treated according to this invention, or with a control, non-fermented cow's milk agent.
Figure 2B:
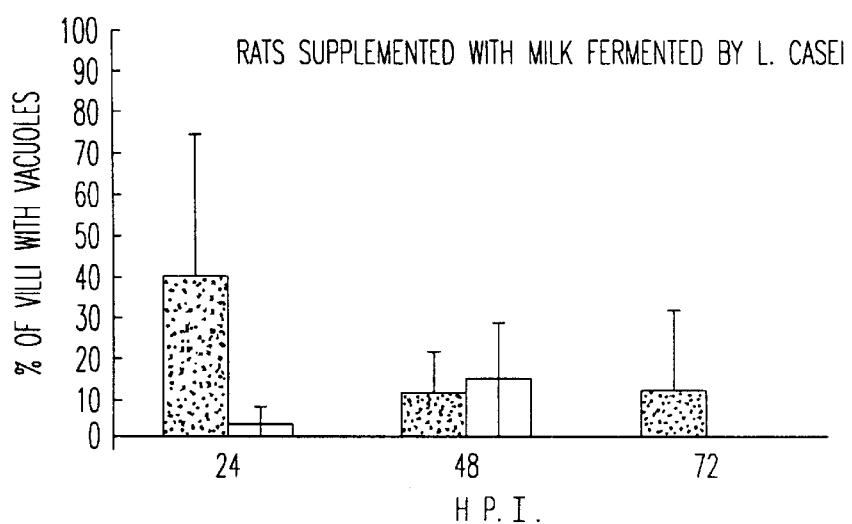

Control section of the group CM presented cells characterized by nuclei localized at their base and by a large supra nuclear area occupying almost the whole apical cytoplasm. In the group RM, histological changes associated with rotavirus infection were characterized by cellular vacuolation. The vacuolation rate of intestinal villi was significantly higher in the group RM compared to the group CM at 2 and 3 days p.i. (FIG. 2). In the group RM, 90, 70 and 16% of the villi presented vacuolation respectively at 2, 3 and 4 days p.i. Whereas in the group CM, vacuolation was observed in less than 10% of the villi throughout the study. An apparent migration of the vacuoles was observed from the basal to the apical area of the villi in the group RM. At 48 h p.i., the cellular vacuoles were located at the basal area of the villi then, they were observed at the tip of the villi at 72 h p.i. The comparison of the 2 infected groups RF and RM showed that the vacuolation rate was significantly lower in the group receiving the fermented milk 48 and 72 h p.i. ($p<0.05$). In both groups receiving the fermented milk RF and CF, the vacuolation rate was not significantly different except at 48 h p.i. However, at this time point the individual variability was large in the group RF: 1 rat out of 3 presented vacuolation in 80% of the villi whereas the 2 others presented a milk vacuolation rate (30% and 10%). These vacuoles were found principally at the basal area of the villi. No significant difference was found between the control groups CF and CM.

Figure 3A:
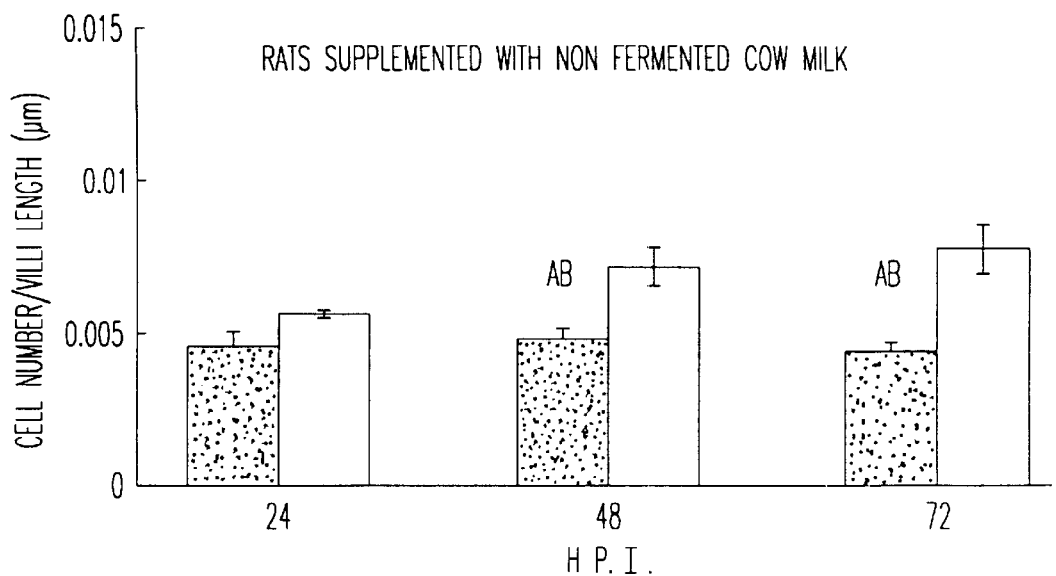
FIG. 3 is a graphic representation of the relative numbers of sulfated mucin containing cells in the small intestine of treated and non-treated model suckling rats.
Figure 3B:
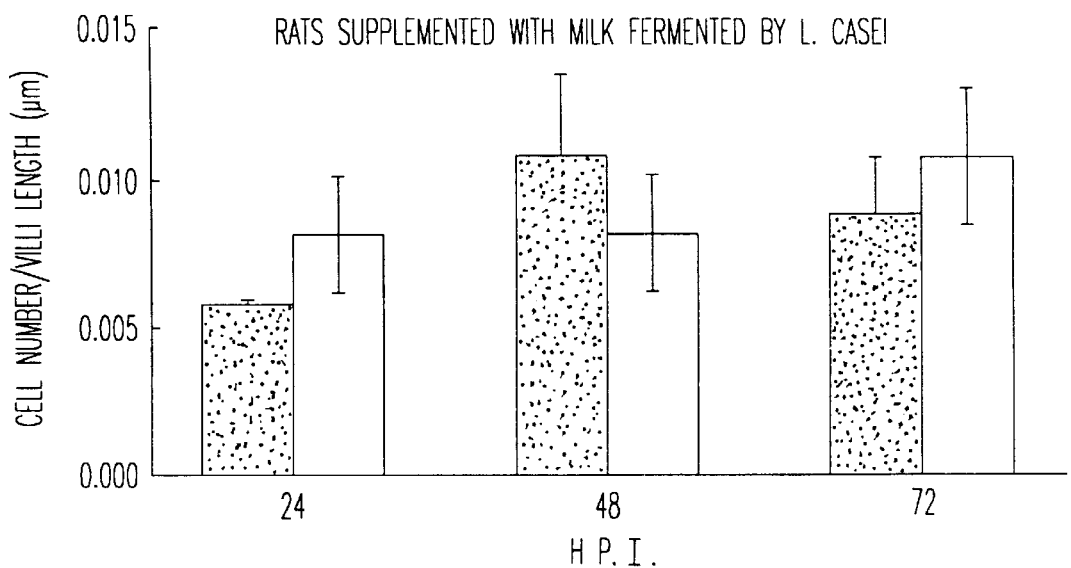

The villi length and the crypt depth were not changed by rotavirus infection, neither by fermented milk supplementation so that parameters expressed relatively to these criteria were comparable. The general morphology of intestinal villi determined by the villi length/crypt depth comparison and the total number of mucus containing cell/villi length ratio was similar between all groups at each time point. However, the number of sulfated mucin containing cells/villi length ratio was significantly lower in the group RM compared to the groups CM and RF, 72 and 96 h p.i. (FIG. 3). For this parameter, no significant difference was observed between the groups supplemented with the fermented milk CF and RF, neither between the 2 control groups CF and CM. No significant effect of infection nor of supplementation was obtained for the number of acid and neutral mucin containing cells.

Clinical Trials

Dual trials involving two parallel groups of children (total 928) of ages 6–24 months were conducted in 49 nursery day care centers. Children consumed 125 ml of L-casei fermented milk per day present, (the control was an equal amount of yoghurt). The inventive product was demonstrated to be statistically superior in preventing and treating diarrhea in infants.

Discussion

The present investigation confirmed our previous findings that have demonstrated that diarrhea occurs in germ-free suckling rats infected with a group A rotavirus strain (17). Five-day-old pups infected with SA11 rotavirus, and daily supplemented with non fermented milk, presented a 6 day diarrhea. In the present study we found that rotavirus infected the epithelium of both the small intestine and the colon. Rotavirus infection in the small intestine has been commonly described in different animal species (22–26). Infection of the colon has been shown in previous observations in infant mice (27, 28).

The mechanisms of rotavirus associated diarrhea are not fully understood. It has been suggested that cellular alterations in the small intestine would play a role in rotavirus associated diarrhea (29). Vacuoles were located at the basal area of the intestinal villi at 2 days p.i., then they were observed at the apical area of the villi. Cellular vacuolation has been associated with rotavirus gastroenteritis in several animal models (26, 30, 31). Rotavirus is thought to infect the differentiated cells at the tip of the intestinal villi. The presence of vacuoles at the basal area at the beginning of the diarrheal period may be explained by the hypothesis proposed recent by Ball et al. (32). The authors have described an enterotoxin-like effect of NSP4, one of the non structural proteins of rotavirus. According to this hypothesis, rotavirus particles would bind some cells, resulting in virus entry and gene expression at the tip of the villi. Then, NSP4 expressed in infected cells, would be released into the lumen and would interact with a specific receptor on adjacent cells. This last interaction would augment the endogenous secretory pathway and induce diarrhea. The "migration" of the vacuoles from the basal to the apical area of the intestinal villi within 24 h is in concordance with the enterocytes turn-over time in the small intestine of suckling rats (33). The enterocytes migration may lead t the release of infected cells into the lumen. In our study, rotavirus antigens were detected in the small intestine during at least 5 days p.i. This data may result from re-infection of the intestinal villi throughout the digestive tract by the virus present in the lumen. This hypothesis is supported by the fact that rotavirus infection progresses from the proximal to the distal area of the small intestine (34).

Watery diarrhea associated with rotavirus infection has been also explained by malabsorption of nutrients following histological lesions. A deficiency in intestinal lactate during rotavirus gastroenteritis has been described in mice (35, 36) and in infants (37). Our results suggest that a release of sulfated mucus may also contribute to fecal emission.

Our results demonstrate that early supplementation with milk fermented by L. casei DN 114-001 had a protective effect on both diarrheal symptoms in suckling rats. The intensity and the duration of feces emission obtained immediately upon palation was shorter in them group RF compared with the group RM. Furthermore, the amount, the duration and the incidence of rotavirus shedding was decreased in the group RF. These results are in agreement with previous studies investigated in rotavirus suffering infants supplemented with Lactobacillus strains. The mean duration of diarrhea has been decreased in infants daily supplemented with L. casei GG as a fermented milk (10, 14) or a freeze-dried powder (13, 15, 38). Similar results have been obtained in diarrheal infants supplemented with L. reuteri (15). The duration and incidence of rotavirus shedding has been decreased in infants receiving the association B. bifidum and S. thermophilu (12). Few experimental studies in animals have been conducted on the protective effect of LAB consumption against rotavirus diarrhea. Duffy et al. (39) have demonstrated in mice infected with a murine rotavirus strain that rotavirus shedding has been reduced and the onset of diarrhea has been delayed by daily gavage with B. bifidum. In their experiments, the duration of diarrhea has not been influenced by B. bifidum supplementation. Our study showed that the percentage of feces obtained from the control group CF were higher than those obtained from the group CM and similar to those from the group RF. This result may be due to the higher amount of material contained int he intestine of the supplemented rats, as demonstrated by the amount of lactobacilli recovered in the colon, rather than a "diarrheal-like" effect of the fermented milk.

The milk fermented by L. casei DN 114-001 did not totally avoid infection in the enterocytes. However our results showed that histopathological changes of the small intestine were significantly reduced in the group RF compared to the group RM. Moreover in rats supplemented with the fermented milk, rotavirus infection was not observed in the colonic epithelium, where the lactobacilli concentration was the highest. It has been suggested that the mucus integrity may be reinforced by probiotics consumption. Isolauri et al. (40) have demonstrated that L. casei GG alleviated the increase in macromolecule absorption during gastroenteritis in suckling rats infected with a group B rotavirus. However it is not known in what way lactobacilli may play a role in this protection. By contrast, Cartwright et al. (30) have demonstrated that administration of Saccharomyces boulardii, commonly used against digestive disorders, did not influence the histopathological changes associated with rotavirus infection in the small intestine of suckling mice.

Previous studies have reported an adjuvant effect of L. casei GG consumption on the immune response in infants infected with rotavirus during the convalescence period, while the symptoms were reduced during the acute phase of diarrhea (41, 42). Isolauri et al. (43) have demonstrated in healthy infants that L. casei GG administration has an immunostimulating effect on oral rotavirus vaccination 8 days post vaccination. However, it is not well established in what way Lactobacillus consumption may play a protective role immediately during the diarrheal period. The survival of the ingested bacterial strains in the digestive tract may be an important factor to produce its effect in vivo. In our study, L. casei DN 114-001 survived throughout the intestinal tract of germ-free suckling rats. This demonstrates that regular consumption of milk fermented with L. casei DN 114-001 may participate to dietary management against rotavirus diarrhea. Further investigations are necessary to determine the mechanisms involved in this protection.

REFERENCES

1. Glass R I, Gentsch J R, Ivanoff B. New Lessons for rotavirus vaccines. *Science* 1996; 272: 46–48.
2. Burns J W, Greenberg H B. Viral gastroenteritis. *Infect. Dis. Clin. Pract.* (Baltim. Md.) 1994; 3: 411–417.
3. Davidson G P, Goodwin D, Robb T A. Incidence and duration of lactose malabsorption in children hospitalized with acute enteritis: study in a well-nourished urban population. *J. Pediatr.* 1984; 105: 587–590.
4. Beau J P, Fontaine O, Garenne M. Management of malnourished children with acute diarrhoea and sugar intolerance. *J. Trop. Pediat.* 1990; 36: 86–89.
5. Reddy N R, Roth S M, Eigel W N, Pierson M D. Foods and good ingredients for prevention of diarrheal disease in children in developing countries. *J. Food Prot.* 1988; 51: 66–75.
6. Bhan M K, Sazawal S, Bhatnagar S, Jailkhani B L, Arora N K. Efficacy of yoghurt in comparison to milk in malnourished children with acute diarrhea. In Syndifrais, ed. *Les laits fermentes. Actualite de la recherche.* Montrouge (FRA): JOhn Libbey Eurotext, 1989: 233–239.
7. Nizami S Q, Bhutta Z A, Molla A M. Efficacy of traditional rice-lentil-yogurt diet, lactose free milk protein-based formula and soy protein formula in management of secondary lactose intolerance with acute childhood diarrhoea. *J. Trop. Pediat.* 1996; 42: 133–137.
8. Brunser O, Araya M, Espinoza J, Guestry P R, Secretin M C, Pacheco I. Effect of an acidified milk on diarrhoea and the carrier state in infants of low socio-economic stratum. *Acta Paediatr. Scand.* 1989; 78: 259–264.
9. Singh T. Yoghurt Feeding during acute diarrhea. *Ind. Pediatr.* 1987; 24: 530.
10. Kaila M, Isolauri E, Soppi E, Virtanen E, Laine S, Arvilommi H. Enhancement of the circulation antibody secreting cell response in human diarrhea by a human Lactobacillus strain. *Pediatr. Res.* 1992; 32: 141–144.
11. Guerin-Danan C, Andrieux C. Nutritional and health benefits of fermented milks by young infants. *Cah. Nutr. Diet.* 1998 (in press).
12. Saavedra J M, Bauman N A, Oung I, Perman J A, Yolken R H. Feeding of *Bifidobacterium bifidum* and *Streptococcus thermophilus* to infants in hospital for prevention of diarrhoea and shedding of rotavirus. *Lancet* 1994; 344: 1046–1049.
13. Guarino A, Canani R B, Spagnuolo M I, Albano F, Benedetto L D. Oral bacterial therapy reduces the duration of symptoms and of viral excretion in children with mild diarrhea. *J. Pediat. Gastroenterol. Nutr.* 1997; 25: 516–519.
14. Isolauri E, Juntunen M, Rautanen T, Sillanaukee P, Koivula T. A human Lactobacillus strain (*Lactobacillus casei* sp strain GG) promotes recovery from acute diarrhea in children. *Pediatrics.* 1991; 88: 90–97.
15. Shornikova A V, Casas I A, Isolauri E, Mykkanen H, Vesikari T. Lactobacillus reuteri as a therapeutic agent in acute diarrhea in young children. *J. Pediat. Gastroenterol. Nutr.* 1997; 24: 399–404.
16. Romond C, Romond M B. Les effets du Bifidobacterium dans les diarrhees: approches des mecanismes d'action. In Syndifrais, ed. Les laits fermentes. Actualite de la recherche, 1989. John Libbey Eurotext, Montrouge, France, p:215–222.
17. Guerin-Danan C, Meslin J C, Lambre F, Charpilienne A, Serezat M, Bouley C, Cohen J, Andrieux C. Development of a heterologous model in germ-free suckling rats for studies on rotavirus diarrhea. *J. Virol* (in press).
18. Reinert P, Leroux M C, N'Guyen O, Gaudichon C. Influence de la consonmmation de laits fermentes au *Lactobacillus casei* (Danone strain 001) sur les diarrhees de l'enfant sain en creche. *Arch. Pediatr.* 1996; 3: 1291.
19. Jourdan N, Maurice M, Delautier D, Quero A M, Servin A, Trugnan G. Rotavirus is released from the apical surface of cultured human intestinal cells through nonconventional vesicular transport that byphases the golgi apparatus. *J. Virol.* 1997; 71: 8268–8278.
20. Kohli E, Maurice L., Vautherot J P, Bourgeois C, Bour J B, Cohen J, Pthier P. Localization of group-specific epitopes on the major capsid protein of group A rotavirus. *J. Gen. Virol.* 1992; 73: 907–914.
21. Sainte-Marie G. A paraffm embedding technique for studies employing immunofluorescence. *J. Histochem. Cytochem.* 1962; 10: 250–256.
22. Salim A F, Phillips A D, Walker-Sniith J A, Farthing M J G. Sequential changes in small intestinal structure and function during rotavirus infection in neonatal rats. *Gut.* 1995; 36: 231–238.
23. Burns J W, Krishnaney A A, Vo P T, Rouse R V, Anderson L J, Greenberg H B. Analyses of homologous rotavirus infection in the mouse model. *Virology.* 1995; 207: 143–143.
24. Majerowicz S, Kubelka C F, Stephens P, Barth O M. Ultrastructural study on experimental infection of rotavirus in a murine heterologous model. *Mem. Inst. Oswaldo Cruz.* 1994; 89: 395–402.
25. Mebus C A, Newman L E. Scanning electron, light, and immunofluorescent microscopy of intestine of gnotobiotic calf infected with reovirus-like agent. *Am. J. Vet. Res.* 1977; 38: 553–558.
26. Johnson C A, Snider T G, Henk W G, Fulton R W. A scanning and transmission electron microscopic study of rotavirus-induced intestinal lesions in neonatal gnotobiotic dogs. *Vet. Pathol.* 1986; 23: 443–453.
27. Banfield W G, Kasnic G, Blackwell J H. Further observations on the virus of epizootic diarrhea of infant mice: an electron microscopic study. *Virology* 1968; 36: 411–417.
28. Wilsnack R E, Blackwell J H, Parker J C. Identification of an agent of epizootic diarrhea of infant mice by immuno-fluorescent and complement-fixation tests. *Am. J. Vet. Res.* 1969; 30: 1195–1204.
29. Superti-F, Ammendolia-M G, Tinari-A, Bucci-B, Gianinarioli-A M, Rainaldi-G, Rivabene-R, Donelli-G. Induction of apoptosis in HT-29 cells infected with SA-11 rotavirus. *J. Med. Virol.* 1996; 50: 325–34.
30. Cartwright-Shamoon J, Dickson G R, Dodge J, Carr K E. Uptake oy yeast (*Saccharomyces boulardii*) in normal and rotavirus treated intestine. *Gut* 1996; 39: 204–209.
31. Heyman M, Corthier G, Petit A, Meslin J C, Moreau C, Desjeux J F. Intestinal absorption of macromolecules during viral enteritis: an experimental study on rotavirus-infected conventional and germ free mice. *Pediatr. Res.* 1987; 22: 72–78.
32. Ball J M, tian P, Zeng C Q Y, Morris A P, Estes M K. Age-dependent diarrhea induced by a rotaviral non-structural glycoprotein. *Science* 1996; 272: 101–104.

33. Trahair J F. Remodeling of the small intestinal mucosa during the suckling period. *J. Pediatri. Gastroenterol. Nutr.* 1989; 9: 232–237.

34. Little L M, Shadduck J A. Pathogenesis of rotavirus infection in mice. *Infect. Immun.* 1982; 38: 755–763.

35. Collins J, Candy D C A, Starkey W G, Spencer A J, Osborne M P, Stephen J. Disaccharidase activities in small intestine of rotavirus-infected suckling mice: a histochemical study. *J. Pediatr. Gastroenterol. Nutr.* 1990; 11: 395–403.

36. Kanwar S S, Singh V, Vinayak V K, Malik A K, Mehta S K, Mehta S. Differential tropism of EB rotavirus (serotype 3) to small intestine of homologous murine model. *Acta Virol.* 1994; 38: 269–276.

37. Davidson G P, Barnes G L. Structural and functional abnormalities of small intestine in infants and young children with rotavirus enteritis. *Acta Paediatr. Scand.* 1979; 68: 181–186.

38. Isolauri E, Kaila M, Mykkanen H, Ling W H, Salminen S. Oral bacteriotherapy for viral gastroenteritis. *Dig. Dis. Sci.* 1994; 39: 2595–2600.

39. Duffy L C, Zielezny M A, Riepenhoff-Talty M, Dryja D, Sayahtaheri-Altaie S, Griffiths E, Ruffin D, Barrett H, Rossman J, Ogra P. Effectiveness of *Bifidobacterium bifidum* in mediating the clinical course of murine rotavirus diarrhea. *Pediatr. Res.* 1994; 35: 690–695.

40. Isolauri E, Joensuu J, Suomalainen H, Luomala M, Vesikari T. Improved immunogenicity of oral D8RRV reassortant rotavirus vaccine by *Lactobacillus casei* GG. *Vaccine* 1995; 13: 310–312.

41. Kaila M, Isolauri E, Arvilomnui H, Vesikari T. Viable versus inactivated Lactobacillus strain GG in acute rotavirus diarrhoea. *Arch. Dis. Child.* 1995; 72: 51–53.

42. Majamaa H, Isolauri E, Saxeline M, Vesikari T. Lactic acid bacteria in the treatment of acute rotavirus gastroenteritis. *J. Pediatr. Gastroenterol. Nutr.* 1995; 20: 333–338.

43. Isolauri E, Kaila M, Arvola T, Majamaa H, Rantala I, virtanen E, Arvilommi H. Diet during rotavirus enteritis affects jejunal permeability to macromolecules in sukling rats. *Pediatr. Res.* 1993; 33: 548–553.

TABLE 1

Rotavirus load/relative concentration (log(CFU/g)) and incidence of viral detection in intestinal segments of germ-free suckling rats. Pups were daily supplemented with non fermented cow milk (RM) or with milk fermented by *L. casei* DN 114-001 (RF) from 2 days of age. They were infected at 5 days of age with SA11 rotavirus. Two to 3 rats were sacrificed at each time point. Rotavirus antigens were detected by ELISA test.

|  | Stomach | | Small intestine | | Colon | |
| --- | --- | --- | --- | --- | --- | --- |
| hp.i. | RM | RF | RM | RF | RM | RF |
| 0 | 7,6 | 7,6 | 6,9 | 6,9 | ND | ND |
|  | (2/2) | (3/3) | (1/2) | (3/3) | (2/2) | (3/3) |
| 3 | ND | 7,1 | 7,3 | 7,3 | 6,7 | ND |
|  | (3/3) | (2/3) | (3/3) | (3/3) | (1/3) | (3/3) |
| 6 | ND | 6,8 | 6,7 | 7,8 | 6,4 | 6,9* |
|  | (3/3) | (1/3) | (2/3) | (3/3) | (2/3) | (1/3) |
| 9 | ND | 7,4 | 7,1 | 7,1 | 7,1 | ND |
|  | (3/3) | (1/3) | (3/3) | (2/3) | (1/3) | (3/3) |
| 12 | ND | ND | 7,2 | ND | 7,3 | ND |
|  | (3/3) | (3/3) | (3/3) | (3/3) | (3/3) | (3/3) |
| 24 | ND | ND | 6,9 | 7,4 | 7,6 | 7,4* |
|  | (3/3) | (3/3) | (3/3) | (3/3) | (1/3) | (3/3) |
| 48 | ND | 7,6 | 7,8 | ND | ND | ND |
|  | (3/3) | (1/3) | (1/3) | (3/3) | (3/3) | (3/3) |
| 72 | ND | ND | 7,4 | ND | ND | 8,4* |
|  | (3/3) | (3/3) | (2/3) | (3/3) | (3/3) | (1/3) |
| 96 | ND | ND | 7,5 | ND | ND | ND |
|  | (3/3) | (3/3) | (2/3) | (3/3) | (3/3) | (3/3) |
| 120 | 7,3 | ND | 7,6 | 7,3 | 7.6 | ND |
|  | (1/2) | (3/3) | (2/2) | (1/3) | (1/2) | (3/3) |

ND not detected
*Rotavirus detected in intestinal content only

TABLE 2

Rotavirus shedding in infected groups supplemented with non fermented cow milk (RM) or milk fermented by *L. casei* DN 114-001 (RF). Rotavirus load was determined on positive samples by ELISA according to a standard curve (log(PFU/ml)). The OD cuttof value was 0.1.

|  | Rotavirus load/relative concentration | | Positive samples | |
| --- | --- | --- | --- | --- |
| hp.i. | RM | RF | RM | RF |
| 24 | 8.9 (± 0.3) | 8.3* (± 0.5) | 14/26 | 6/16 |
| 48 | 8.4 (± 0.5) | 7.9 (± 0.8) | 13/24 | 5/21** |
| 72 | 8.0 (± 0.5) | 6.9* (± 0.5) | 6/31 | 5/23 |
| 96 | 8.4 (± 0.5) | 7.4 (± 1.0) | 4/27 | 5/17 |
| 120 | 7.9 (± 0.5) | 7.6 (± 0.2) | 6/21 | 2/10 |
| 144 | 9.1 | / | 1/13 | 0/5 |
| 168 | / | / | 0/3 | 0/4 |

*The rotavirus load was significantly lower in the group RF compared to the group RM ($P < 0.05$).
**The proportion of positive samples was significantly lower in the group RF compared to the group RM ($P < 0.05$).

This invention has been demonstrated by generic disclosure, and specific embodiment. Specific embodiments are not intended to be limiting, and variations will occur to those of ordinary skill in the art, particularly with respect to the nature of the fermented milk product, the period of its administration, concentration and amounts. These variations, and others, remain within the scope of the invention, unless delimited by the recitation of the claims set forth below.

What is claimed is:

1. A method of supplementing the nutrition of an infant up to 24 months of age so as to reduce the frequency and severity of rotavirus-associated diarrhea therein, comprising administering to an infant up to 24 months of age in need thereof an effective amount of a milk product fermented with a bacterial agent consisting of *L. casei* DN 114-001, wherein the milk product contains at least $10^6$ CFU/g *L. casei* strain DN 114-001.

2. The method of claim 1, wherein said amount is at least $10^8$ CFU/g.

3. The method of claim 1, wherein said fermented milk product is administered to said infant on a daily basis.

4. The method of claim 1, wherein said fermented milk product is administered to said infant periodically, with the period varying from 1–7 days.

5. A method of treating a rotavirus-associated diarrhea episode in an infant, comprising administering to said infant, on a daily basis beginning with the onset of said diarrhea episode, a milk product fermented with a bacterial agent consisting of *L. casei* DN 114-001, in an amount effective to reduce at least one of the severity and duration of said diarrhea episode.

6. A method for treating rotavirus-associated diarrhea comprising:
   administering an effective amount of a fermentation product fermented with a bacterial agent consisting of *L. casei* strain DN 114-001 to a subject in need thereof, wherein the fermentation product contains at least $10^6$ CFU/g *L. casei* strain DN 114-001.

7. The method of claim 6, wherein said fermentation product comprises a milk product.

8. The method of claim 6, wherein said subject is an infant 24 months in age or less.

9. The method of claim 6, wherein said fermentation product contains at least $10^8$ CFU/g *L. casei* strain DN 114-001.

10. The method of claim 6, wherein said fermentation product contains at least $10^{10}$ CFU/g *L. casei* strain DN 114-001.

11. A method for treating rotavirus-associated diarrhea comprising:
    administering an effective amount of a composition consisting essentially of *L. casei* strain DN 114-001 to a subject in need thereof,
    wherein said composition contains at least $10^6$ CFU/g of *L. casei* strain DN 114-001, and
    wherein said composition does not contain *Streptomyces thermophilus* DN-001 147, *Streptococcus thermophilus* DN-001 339 and *Lactobacillus bulgaricus* DN-100 182.

12. A composition comprising:
    an infant formula, and
    a milk product fermented with a bacterial agent consisting essentially of *L. casei* DN 114-001,
    wherein said composition contains at least $10^6$ CFU/g of *L. casei* strain DN 114-001, and
    wherein said composition does not contain *Streptomyces thermophilus* DN-001 147, *Streptococcus thermophilus* DN-001 339 and *Lactobacillus bulgaricus* DN-100 182.

13. The composition of claim 12, wherein said composition contains at least $10^8$ CFU/g of *L. casei* strain DN 114-001.

14. The composition of claim 12, wherein said composition contains at least $10^{10}$ CFU/g of *L. casei* strain DN 114-001.

15. A composition comprising:
    an infant formula, and
    a milk product fermented with a bacterial agent that consists of *L. casei* DN 114-001,
    wherein said composition contains at least $10^6$ CFU/g of *L. casei* strain DN 114-001.

* * * * *

UNITED STATES PATENT AND TRADEMARK OFFICE
CERTIFICATE OF CORRECTION

PATENT NO.     : 6,399,055 B1                                        Page 1 of 1
DATED          : June 4, 2002
INVENTOR(S)    : Postaire et al.

It is certified that error appears in the above-identified patent and that said Letters Patent is hereby corrected as shown below:

<u>Title page,</u>
The CPA information has been omitted. Item [45] and the Notice information should read as follows:

-- [45] Date of Patent: *Jun. 4, 2002

[*] Notice: This patent issued on a continued prosecution application filed under 37 CFR 1.53(d), and is subject to the twenty year patent term provisions of 35 U.S.C 154(a)(2).

Subject to any disclaimer, the term of this Patent is extended or adjusted under 35 U.S.C 154(b) by 0 days. --

Signed and Sealed this

Fifth Day of November, 2002

Attest:

Attesting Officer

JAMES E. ROGAN
*Director of the United States Patent and Trademark Office*